(12) United States Patent
Richard (10) Patent No.: US 9,101,435 B2
(45) Date of Patent: Aug. 11, 2015

(54) PACKAGING DEVICE FOR A DENTAL IMPLANT

(71) Applicant: ANTHOGYR, Sallanches (FR)

(72) Inventor: Hervé Richard, Notre Dame de Bellecombe (FR)

(73) Assignee: ANTHOGYR, Sallanches (FR)

( * ) Notice: Subject to any disclaimer, the term of this patent is extended or adjusted under 35 U.S.C. 154(b) by 0 days.

(21) Appl. No.: 14/108,415

(22) Filed: Dec. 17, 2013

(65) Prior Publication Data

US 2014/0166508 A1    Jun. 19, 2014

(30) Foreign Application Priority Data

Dec. 19, 2012  (FR) ..................................... 12 62360

(51) Int. Cl.
*A61C 8/00* (2006.01)
*A61C 19/02* (2006.01)

(52) U.S. Cl.
CPC ............... *A61C 8/0087* (2013.01); *A61C 19/02* (2013.01)

(58) Field of Classification Search
USPC ......... 206/63.5, 438, 368, 379; 433/141, 173, 433/174
See application file for complete search history.

(56) References Cited

U.S. PATENT DOCUMENTS

| | | | |
|---|---|---|---|
| 6,287,117 B1 * | 9/2001 | Niznick | 433/173 |
| 6,955,258 B2 | 10/2005 | Howlett | |
| 7,451,870 B2 | 11/2008 | Donahoe | |
| 8,083,054 B2 * | 12/2011 | Nihei et al. | 206/63.5 |
| 2010/0243485 A1 * | 9/2010 | Sato et al. | 206/63.5 |
| 2011/0056851 A1 | 3/2011 | Schlottig | |

FOREIGN PATENT DOCUMENTS

| | | |
|---|---|---|
| EP | 2233109 A1 | 9/2010 |
| EP | 2279710 A1 | 2/2011 |
| EP | 2377489 A1 | 10/2011 |
| WO | 2009147166 A1 | 12/2009 |

\* cited by examiner

*Primary Examiner* — Anthony Stashick
*Assistant Examiner* — Robert Poon
(74) *Attorney, Agent, or Firm* — William H. Eilberg (57) ABSTRACT

Packaging device (1) for a dental implant (2), comprising first (10*a*) and second (10*b*) means of lateral retention of the implant (2), which means are respectively fixed to two mutually opposite first lateral parts (11*a*) and (11*b*) of the peripheral lateral wall (4). At least one of the two first lateral parts (11*a*, 11*b*) is movable between a first position, in which the first (10*a*) and second (10*b*) means of lateral retention of the implant (2) are situated at a first distance from each other, and a second position, in which the first (10*a*) and second (10*b*) means of lateral retention of the implant (2) are situated at a second distance from each other, the second distance being shorter than the first distance.

18 Claims, 5 Drawing Sheets

PACKAGING DEVICE FOR A DENTAL IMPLANT

TECHNICAL FIELD OF THE INVENTION

The present invention relates to the field of dental implantology and more particularly relates to a packaging device for a dental implant.

A dental implant is intended to be screwed into the bone of the jaw of the patient and has the general form of an externally threaded cylinder, provided at its upper end with a connection cavity intended to receive a dental prosthesis or an intermediate element for supporting a dental prosthesis.

After extraction of a tooth, the practitioner reams the dental alveolus left empty in the jaw of the patient, into which dental alveolus the dental implant is intended to be fitted by screwing. The geometry of the dental alveolus is never perfect, and therefore the practitioner may be forced to make several attempts at screwing the implant into place and to adapt, if necessary, the shape of the dental alveolus by carrying out successive reaming procedures. Between two successive reaming procedures, the practitioner has to place the dental implant, which he has unsuccessfully attempted to screw in, temporarily back into its package in order to proceed with correcting the dental alveolus.

Several existing packages for a dental implant allow the dental implant to be placed back into its package, for example the one described in the document US 2011/0056851 A1. In the latter document, the dental implant is held via an intermediate piece fitted in the connection cavity of the implant. This intermediate piece is generally called an implant mount. This implant mount allows the implant to be taken hold of and replaced in its package without the practitioner having to touch the implant with his hands, thereby ensuring satisfactory hygiene conditions. However, the use of an implant mount has several disadvantages. First of all, this is an intermediate piece which is intended to be discarded subsequently and which thus needlessly increases the cost of production and sale price of the implant. In addition, the use of an implant mount engaged in the connection cavity of an implant substantially increases the axial size compared to the solution that involves engaging a transporting and screwing tool directly in the connection cavity of the implant. The increase in the axial size is particularly critical when the implant is one intended for replacing a back tooth of the jaw of the patient. The use of an implant mount also extends the operating time, since it has to be dismantled by withdrawing it from the connection cavity of the implant after the latter has been screwed into the jaw of the patient. Finally, since the implant mount generally conceals the top of the implant, the practitioner has a poor view of the depth of engagement of the implant when screwing it into the jaw of the patient.

It is therefore desirable to do without an implant mount and to manipulate the implant with the aid of a single transporting/screwing tool that engages directly in the connection cavity of the implant.

The document US 2005/0023166 A1 describes a package for a dental implant, in which the dental implant is packaged without an implant mount. When opening the package, the connection cavity of the implant is oriented in such a way as to be accessible for the engagement of a transporting/screwing tool. However, in said document, no provision is made for replacing the implant in the packaging device. Indeed, to replace the implant in its package, it is necessary to perform a movement of relative separation by exerting traction between the transporting/screwing tool and the implant. In the case of the packaging device described in the document US 2005/0023166 A1, the practitioner is required to separate the implant from the transporting/screwing tool by taking hold of the transporting/screwing tool with one hand (via his dental handpiece) and holding the dental implant in his other hand. Such a solution is not satisfactory from the point of view of hygiene.

The document US 2007/0181446 A1 describes a packaging device for an implant, having a hollow rigid outer tube into which is inserted a sleeve provided with arms for gripping an implant. The sleeve is mounted rotatably in the hollow tube. Depending on the position of rotation of the sleeve in the hollow tube, the arms are spaced apart to a greater or lesser extent in order to clamp or release a dental implant. For it to function correctly, this packaging device requires a perfectly rigid outer tube, without which the relative position of the gripping arms, and therefore the retention of the implant, would be uncertain. The gripping and the release of the implant are not easy for the practitioner to select in order to allow him to easily replace an implant in the packaging device without having to touch the implant with his hand and without using an implant mount.

The document EP 2 279 710 A1 describes a packaging device according to the preamble of claim 1. This packaging device has internal fins with a deformable free end part for clamping a dental implant. Only the free end of the fins is elastically deformable. For the fins to correctly retain the dental implant, the peripheral lateral wall must be perfectly rigid, failing which the relative position of the free ends of the fins, and therefore the retention of the implant, would be uncertain. The practitioner cannot selectively choose to retain or release a dental implant in the packaging device, in order to permit easy replacement of an implant in the packaging device, without having to touch the implant with his hand and without using an implant mount.

SUMMARY OF THE INVENTION

A problem addressed by the present invention is to design a packaging device for a dental implant, which allows an implant to be easily put back into said packaging device under good conditions of hygiene, without the need to touch the implant with a hand and without using an implant mount.

To achieve these aims, and others too, the invention proposes a packaging device for a dental implant comprising:
  a hollow tube having a peripheral lateral wall, a bottom wall and an opening face, which define an internal compartment,
  a cap intended to close the opening face of the tube,
  first means of axial abutment of the implant in the internal compartment,
  first and second means of lateral retention of the implant, which means are respectively fixed to two mutually opposite first lateral parts of the peripheral lateral wall, in which at least one of the two first lateral parts is movable between a first position, in which the first and second means of lateral retention of the implant are situated at a first distance from each other, and a second position, in which the first and second means of lateral retention of the implant are situated at a second distance from each other, the second distance being shorter than the first distance.

In order to separate the implant from the transporting/screwing tool, after the introduction of the dental implant into the internal compartment of the hollow tube (the dental implant being press-fitted on the transporting/screwing tool), the practitioner moves the two first lateral parts from their first position to their second position in order to bring the first and second means of lateral retention of the implant up against the dental implant, in such a way as to clamp the latter radially. The practitioner can then exert a separating force by pulling axially on the transporting/screwing tool, the implant being retained by clamping in the hollow tube of the packaging device. During such an operation, the practitioner does not touch the implant with his hands.

Advantageously, the peripheral lateral wall can be continuous, such that closure of the opening face defines a closed internal compartment. A continuous peripheral lateral wall effectively limits the risks of contamination of the implant once the latter has been put back into its packaging.

Preferably, it can be provided that:
the two mutually opposite first lateral parts have a first rigidity,
the peripheral lateral wall has second lateral parts that have a second rigidity less than the first rigidity and that are designed and arranged in such a way as to allow the two first lateral parts to move toward and/or away from each other.

The second lateral parts thus permit a relative movement of the first lateral parts toward and/or away from each other, even if the peripheral lateral wall is continuous.

Advantageously, the packaging device can have elastic return means for returning the two first lateral parts to the first position.

The practitioner then only has to press the two first lateral parts toward each other, by exerting a closing force by gripping them between his thumb and his index finger, in order to bring the two first lateral parts to the second position. The return to the first position is automatic after the practitioner relaxes his gripping force. The practitioner thus uses only one of his hands to manipulate the packaging device, the other hand being used to hold the dental handpiece which carries the transporting/screwing tool.

Advantageously, the bottom wall and the two first lateral parts can be formed in one piece. It is thus easy to manufacture a one-piece "clamp" incorporating the elastic return means for returning the two first lateral parts to the first position.

Advantageously, the packaging device can have interlocking means between the first and second lateral parts in order to obtain a continuous peripheral lateral wall after interlocking. An interlocking is a reliable connection for ensuring satisfactory sealing between the internal compartment and the outside of the packaging device.

In practice, the first or second lateral parts can have an interlocking groove, while the others of the first or second lateral parts have an interlocking rib.

Advantageously, the second lateral parts can be in the form of tongues integrally connected to a ring, which is intended to laterally cover upper free ends of the first lateral parts. The tongues close the space between two first lateral parts and form the flexible second lateral parts, while the ring limits the spacing between the first lateral parts and thus defines the first distance in the first position of the first lateral parts. Finally, the ring allows the cap to be received with a press fit, which press fit can entail a certain amount of frictional force that ensures a satisfactory retention of the cap.

Preferably, it can be provided that:
the first means of axial abutment of the implant have a support plate,
the packaging device has receiving means for said support plate, which receiving means are designed and arranged in such a way as to receive the support plate at different distances from the opening face.

In this way, one and the same packaging device can receive implants of very different lengths.

In practice, the receiving means can have a plurality of receiving notches arranged on the internal faces of the first lateral parts.

Advantageously, the cap can close the opening face by engaging with force on the hollow tube, and the cap, when it closes the hollow tube, can have a lateral overhang with respect to the peripheral lateral wall of the hollow tube.

Such a connection of the cap on the hollow tube and such a configuration of the cap allow the practitioner to open the packaging device using just one of his hands. In particular, it suffices for the practitioner to take hold of the packaging device in one hand and use one thumb to push the lateral overhang of the cap in order to separate the cap from the hollow tube.

Preferably, at least one of the first lateral parts can have an external groove arranged in line with the lateral overhang of the cap. This external groove permits intuitive gripping of the packaging device in one hand, the practitioner being assured of a good grip when his thumb is engaged in the external groove. The external groove then serves as a guide groove in which the practitioner moves his thumb in order to press against the lateral overhang of the cap and separate the latter from the hollow tube.

Advantageously, the cap can be dimensioned in such a way that, when it closes the opening face of the hollow tube, the cap holds the first and second means of lateral retention of the implant at a distance shorter than the first distance, and preferably equal to the second distance.

The cap is thus engaged with slight force on the hollow tube, which effectively limits the risks of accidental loss of the cap.

Preferably, the cap can have, on its internal lower face, second means of axial abutment, which are designed and arranged in such a way as to oppose escape of the implant from the means of lateral retention.

Thus, during transport thereof, the dental implant is held reliably between the first and second means of axial abutment and the first and second means of lateral retention.

Advantageously, the first and second means of axial abutment and the first and second means of lateral retention are made of a biocompatible material.

It is thus possible to avoid polluting the implant with a material that could risk causing necrosis of the bone after the implant has been screwed into the jaw of the patient. It is particularly expedient to use a material that does not affect the implant (for example by oxidation). To do so, first and second means of axial abutment and first and second means of lateral retention can be provided that are made of the same material as the dental implant, for example of titanium.

Advantageously, the cap can have, on its internal lower face, a receiving seat intended to receive a closure screw for closing the connection cavity of an implant.

BRIEF DESCRIPTION OF THE DRAWINGS

Other subjects, features and advantages of the present invention will become clear from the following description of specific embodiments, with reference being made to the attached figures, in which.

DESCRIPTION OF THE PREFERRED EMBODIMENTS

A specific embodiment of a packaging device 1 according to the invention for a dental implant 2 is shown in FIGS. 1 to 4.

Figure 2:
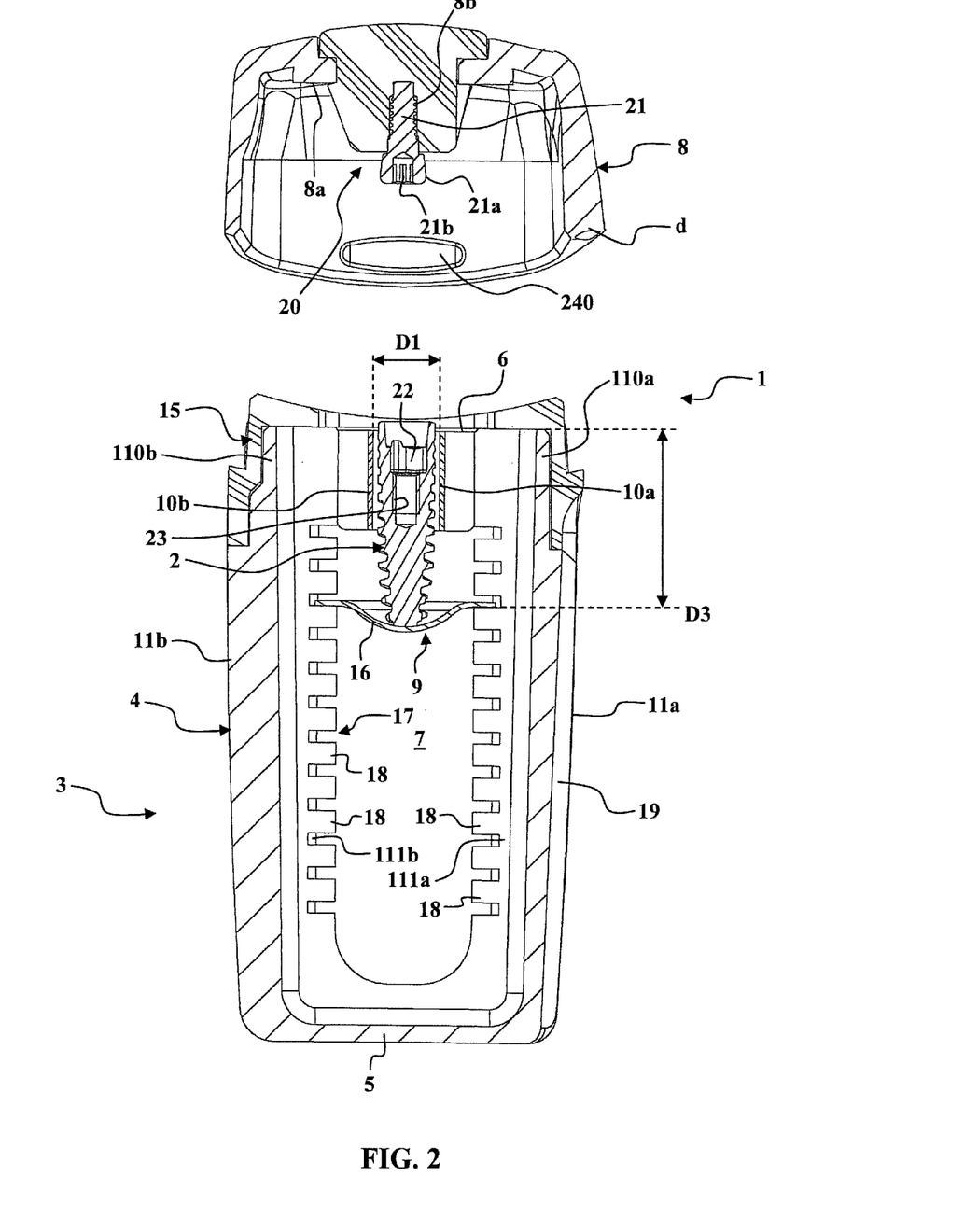
FIG. 2 is a cross-sectional view of the packaging device from FIG. 1, with its cap situated in line with and at a distance from the opening face of the hollow tube.
Figure 3:
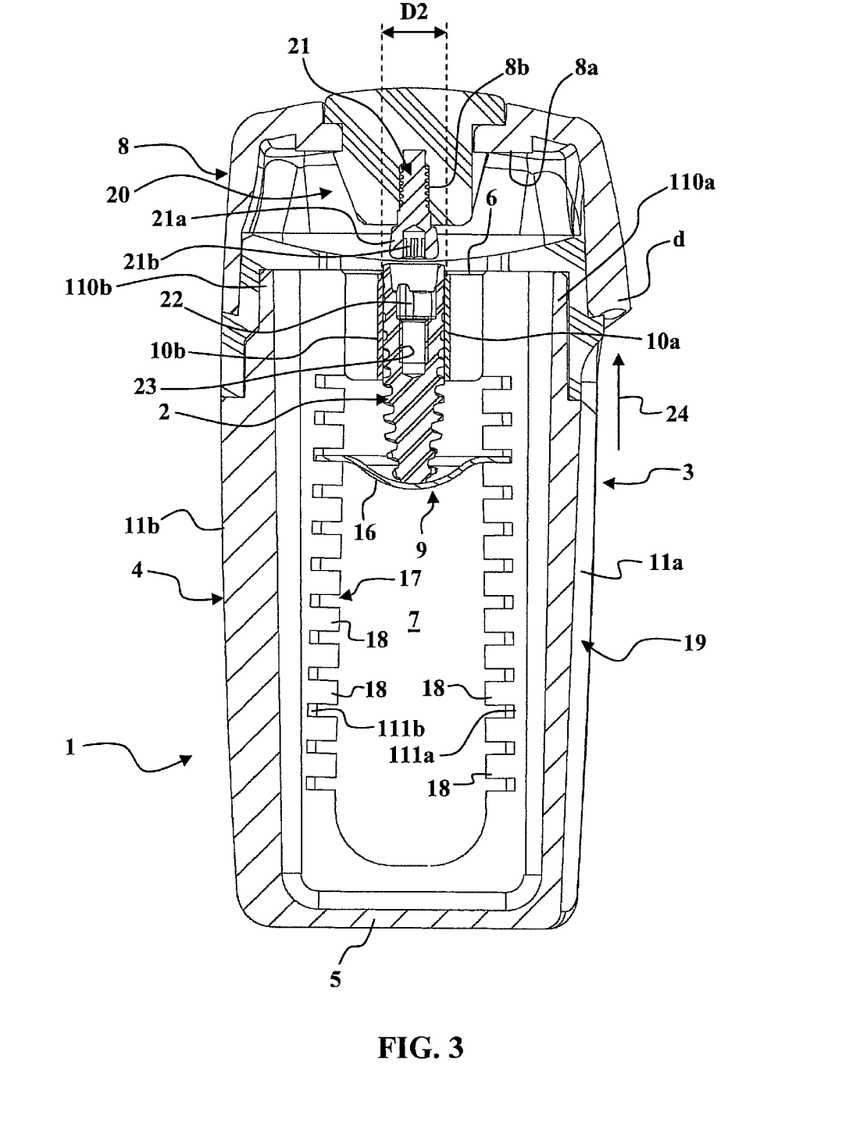
FIG. 3 is a cross-sectional view of the implant from FIG. 2, with the cap closing the hollow tube.
Figure 4:
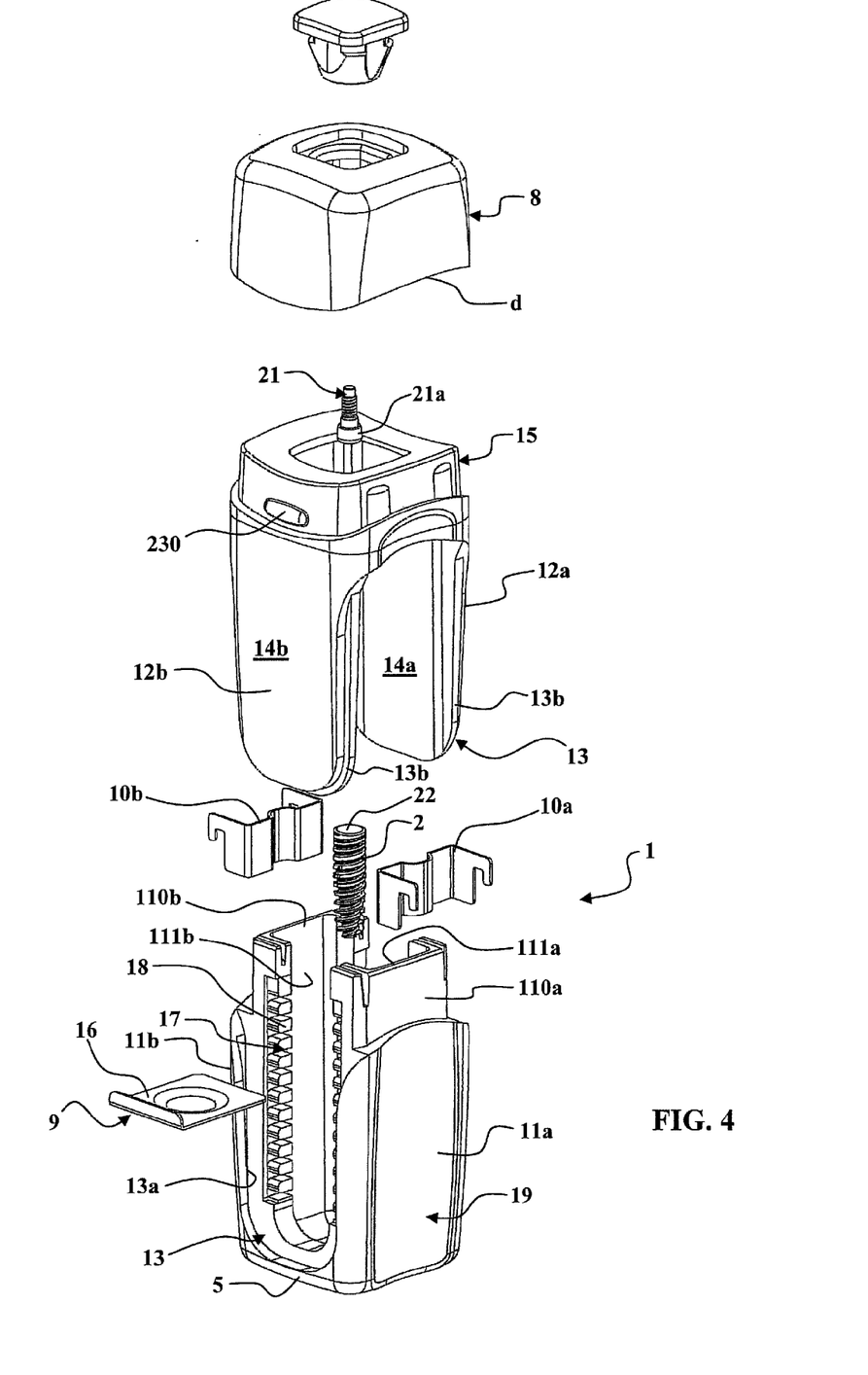
FIG. 4 is an exploded perspective view of the packaging device from FIGS. 1 to 3.

The packaging device 1 has a hollow tube 3 comprising a peripheral lateral wall 4, a bottom wall 5 and an opening face 6, which define an internal compartment 7. The packaging device 1 also comprises a cap 8 intended to close the opening face 6 of the tube 3. In FIGS. 2 to 4, it will be seen that the packaging device 1 also comprises first means of axial abutment 9 of the implant 2 in the internal compartment 7.

First and second means of lateral retention 10a and 10b of the implant 2 are fixed respectively to two mutually opposite first lateral parts 11a and 11b of the peripheral lateral wall 4.

As is shown more particularly in FIGS. 2 and 3, the first lateral parts 11a and 11b are movable between a first position (FIG. 2), in which the first and second means of lateral retention 10a and 10b of the implant 2 are situated at a first distance D1 from each other, and a second position (FIG. 3), in which the first and second means of lateral retention 10a and 10b of the implant 2 are situated at a second distance D2 from each other, the second distance D2 being shorter than the first distance D1.

Figure 1:
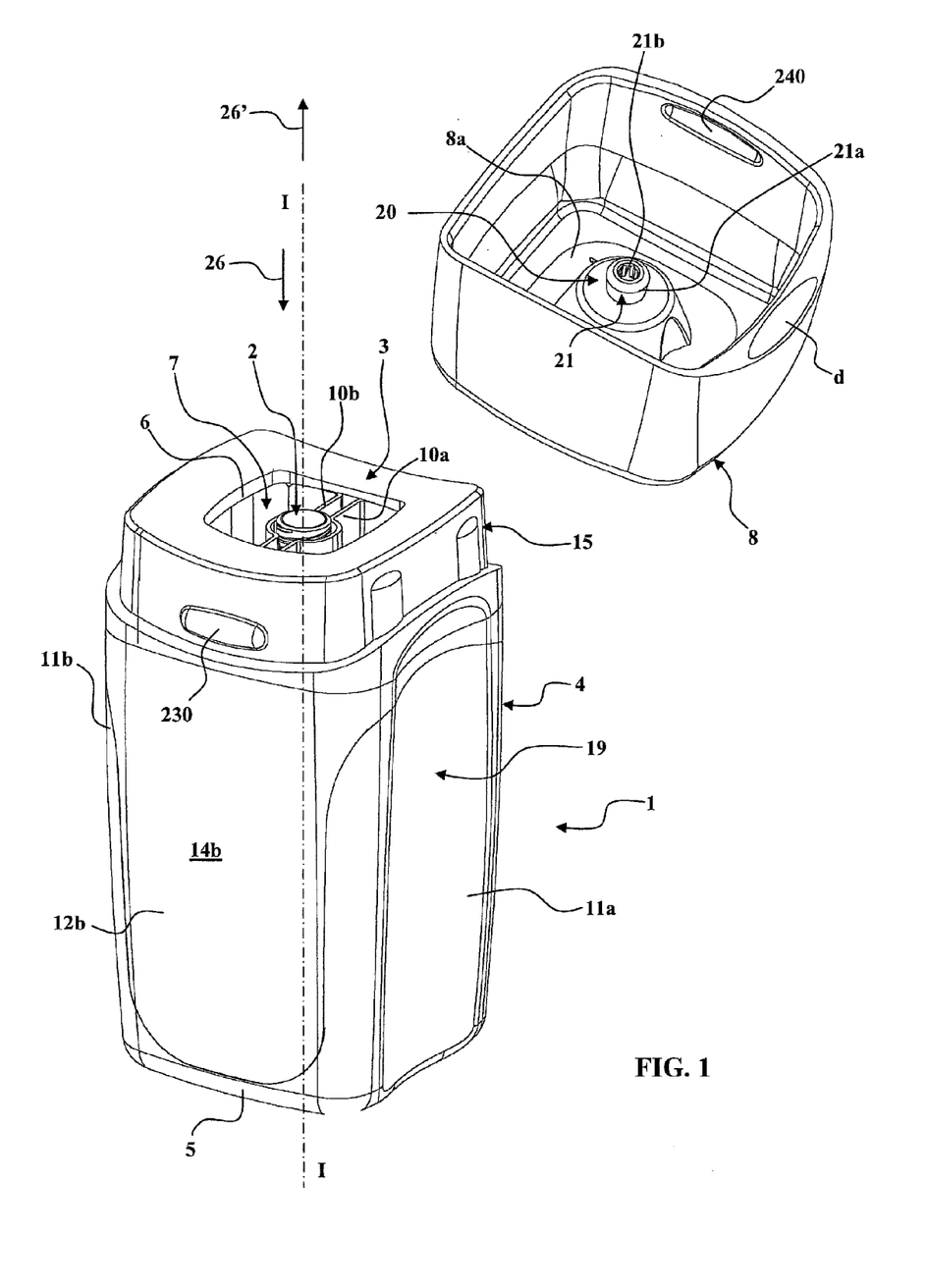
FIG. 1 is a perspective view of a packaging device according to a specific embodiment of the invention, in the open position.

It will be seen more particularly from FIG. 1 that the peripheral lateral wall 4 is continuous, such that the closure of the opening face 6 defines a closed internal compartment 7. To do this, the first lateral parts 11a and 11b are connected to each other by second lateral parts 12a and 12b.

To facilitate the movement of the first lateral parts 11a and 11b toward and/or away from each other, it can be provided that:

the two mutually opposite first lateral parts 11a and 11b of the peripheral lateral wall 4 have a first rigidity, the second lateral parts 12a and 12b of the peripheral lateral wall 4 have a second rigidity less than the first rigidity and are designed and arranged in such a way as to allow the two first lateral parts 11a and 11b to move toward and/or away from each other.

In the case in point, the packaging device 1 has a transverse section with a generally square shape, by means of two first lateral parts 11a and 11b being connected to each other, on either side of the internal compartment 7, by the second lateral parts 12a and 12b.

It will be seen more particularly from FIG. 4 that the bottom wall 5 and the two first lateral parts 11a and 11b are produced in one piece, said piece having the general form of a U-shaped clamp, of which the two parallel branches (here the two first lateral parts 11a and 11b) are elastically returned to the first position. This capacity for elastic return away from each other and/or toward each other is obtained by producing the bottom wall 5 and the two first lateral parts 11a and 11b from a suitable material such as a plastics material, especially a copolymer material, for example.

Still with reference to FIG. 4, it will be seen that the packaging device 1 has means of interlocking 13 between, on the one hand, the first lateral parts 11a, 11b and, on the other hand, the second lateral parts 12a and 12b in order to obtain a continuous peripheral lateral wall 4 after interlocking. In the case in point, the first lateral parts 11a and 11b have an interlocking groove 13a, while the second lateral parts 12a and 12b have interlocking ribs 13b.

The second lateral parts 12a and 12b are in the form of tongues 14a and 14b integrally connected to a ring 15 which is intended to laterally cover the free upper ends 110a and 110b of the first lateral parts 11a and 11b.

The first means of axial abutment 9 of the implant 2 are seen more particularly in FIGS. 2 to 4. They have a support plate 16, and the packaging device 1 has receiving means 17 for said support plate 16, which receiving means 17 are designed and arranged in such a way as to receive the support plate 16 at different distances D3 from the opening face 6. In the case in point, the receiving means 17 have a plurality of receiving notches 18 arranged on the internal faces 111a and 111b of the first lateral parts 11a and 11b.

It will be seen more particularly from FIG. 3 that the cap 8 closes the opening face 6 by engaging with slight force on the hollow tube 3. In the case in point, a simple press-fit is sufficient. The cap 8, when it closes the hollow tube 3, has a lateral overhang d with respect to the peripheral lateral wall 4 of the hollow tube 3. In the case in point, the lateral overhang d protrudes outward with respect to the first lateral part 11a.

The first lateral part 11a also has an external groove 19 arranged in line with the lateral overhang d of the cap 8.

By comparing FIGS. 2 and 3, it will be seen that:

when the cap 8 does not close the hollow tube 3, the first lateral parts 11a and 11b are elastically returned to the first position, when the cap 8 closes the hollow tube 3, the latter moves the first lateral parts 11a and 11b toward each other, such that the first and second means of lateral retention 10a and 10b are situated at a distance shorter than the first distance.

In the case in point, in FIG. 3, the cap 8 holds the first and second means of lateral retention 10a and 10b of the implant 2 at a second distance D2, which allows the implant 2 to be clamped between the first and second means of lateral retention 10a and 10b.

To allow movements of the first lateral parts 11a and 11b toward and/or away from each other, the second lateral parts 12a and 12b are produced from a flexible elastic material, for example an elastomeric material.

It will be seen more particularly from FIGS. 1 to 3 that the cap 8 has, on its internal lower face 8a, second means of axial abutment 20, which are designed and arranged in such a way as to oppose escape of the implant 2 from the means of lateral retention 10a and 10b. To do this, the cap 8 has, on its internal lower face 8a, a receiving seat 8b intended to receive a closure screw 21 for closing the connection cavity 22 of the implant 2.

The closure screw 21 is intended to be screwed into the connection cavity 22 by cooperation with the internal thread 23. When the closure screw 21 is screwed into the internal thread 23, the head 21a of the closure screw 21 seals off the connection cavity 22 of the implant 2.

To avoid any incompatibility between the materials that could lead to degradation (for example by oxidation), it is provided that the implant 2, the closure screw 21, the support plate 16, the means of lateral retention 10a and 10b are made from one and the same biocompatible material, for example titanium.

The use of the packaging device 1 according to the invention will now be explained in more detail.

In the initial state, the packaging device 1 is in the form illustrated in FIG. 3, where the cap 8 closes the opening face 6 of the tube 3. The dental implant 2 is contained in the internal compartment 7 by being retained laterally between the first and second means of lateral retention 10a and 10b and by being held axially between the first and second means of axial abutment 9 and 20. For this purpose, the cap 8 is press-fitted onto the ring 15 which, being made of a flexible elastomeric material, retains the cap 8 with a certain amount of friction. In the present case, bulges 230 are also provided on the ring 15 (FIGS. 1 and 4) and are intended to engage in indentations 240 provided in the cap 8. The implant 2 rests on the support plate 16, and the head 21a of the closure screw 21 is in immediate proximity to, or even bears against, the implant 2. The implant 2 is thus held in the internal compartment 7 with very small degrees of freedom.

After the practitioner has successively drilled a hole in the jaw of the patient with the aid of drill bits mounted on a dental handpiece, he takes hold of the packaging device 1 in just one hand, places a thumb in the external groove 19, then moves this thumb in a movement illustrated by the arrow 24 until said thumb abuts the lateral overhang d in order to apply a force aimed at separating the cap 8 from the hollow tube 3. When this force is applied, the cap 8, which is simply press-fitted onto the tube 3, separates from the tube 3 as shown in FIG. 2, and the practitioner then lets it drop onto a sterile drape in order to maintain good sterility of the cap 8 and of the closure screw 21.

Figures 5, 6:
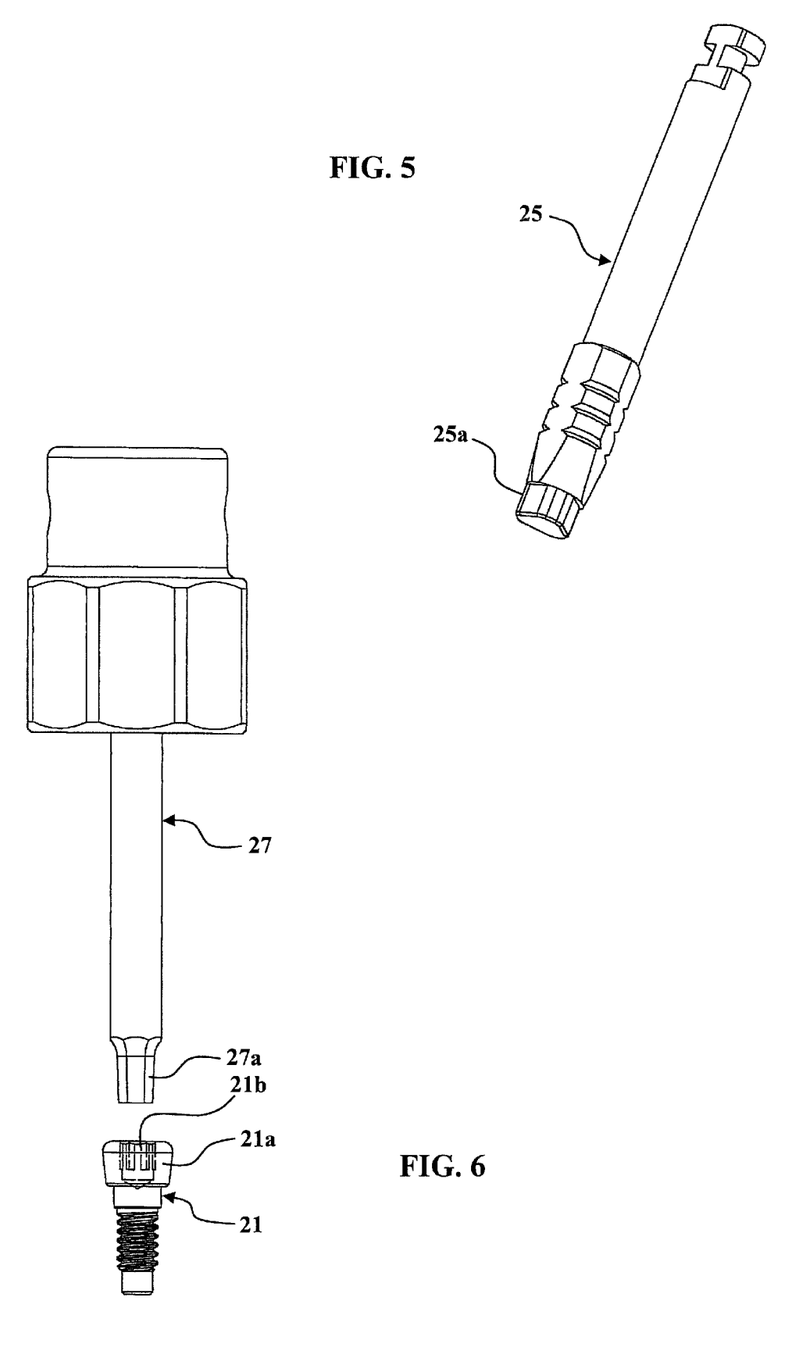
FIG. 5 is a perspective view of a transporting/screwing tool.
FIG. 6 is a side view of a closure screw, for closing the connection cavity of an implant, and of a tool for screwing said screw.

With his other hand, the practitioner takes hold of a dental handpiece, of which the mandrel carries a transporting/screwing tool 25, as illustrated in FIG. 5. The transporting/screwing tool 25 has a distal end 25a of such shape and size as to engage by fitting with slight force in the connection cavity 22 of the implant 2. To do this, the practitioner holds the packaging device 1 as illustrated in FIG. 1, with the opening face 6 directed upward, and then engages the transporting/screwing tool 25 with its distal end 25a into the connection cavity 22, in a translational movement illustrated by the arrow 26.

Having fitted the transporting/screwing tool 25 into the implant 2, the practitioner can withdraw the hand-tool from the packaging device 1 in the axial direction the implant, integral with the transporting/screwing tool 25, then emerges from the packaging device 1 in a translational movement shown by the arrow 26'. The first and second means of lateral retention 10a and 10b are in the first position (FIG. 2) and therefore do not oppose the withdrawal of the implant 2 from the packaging device 1. The practitioner then attempts to screw the implant into the dental alveolus that has been reamed in the jaw of the patient.

If the practitioner is unable to screw the implant satisfactorily into the dental alveolus, he can temporarily re-introduce the implant 2 into the packaging device 1 in the translational movement shown by the arrow 26. The practitioner then grips the packaging device 1 between his fingers in order to move the two first lateral parts 11a and 11b to the second position. The first and second means of lateral retention 10a and 10b then radially clamp the implant 2, and the practitioner is then able to pull slightly on the transporting/screwing tool 25 in order to break the temporary press-fit connection between the transporting/screwing tool 25 and the implant 2. The practitioner can then place the cap 8 back on the packaging device 1, before leaving the latter lying on a sterile drape.

The practitioner proceeds to ream the dental alveolus again with the aid of a drill bit, and he then repeats the operations of connecting the transporting/screwing tool 25 to the implant 2 and screwing the implant into the dental alveolus, of which the geometry has been corrected by further reaming.

During the screwing of the implant 2 into the jaw of the patient, the upper part of the implant, near the connection cavity 22, remains visible, such that the practitioner has a satisfactory way of visually checking the depth of engagement of the implant 2. Once the implant 2 has been screwed into the dental alveolus and is retained in the latter by its external thread, the practitioner pulls the transporting/screwing tool 25 away from the implant 2 in order to break the temporary press-fit connection between these two elements.

The practitioner then proceeds to close the connection cavity 22 of the implant 2. To do this, he uses a screwing tool 27 (FIG. 6) which he engages in the socket 21b of the closure screw 21 still contained in the receiving seat 8b. The distal end 27a of the screwing tool has a slight conicity, in order to fit with slight wedging in the socket 21b. The practitioner then pulls the screwing tool 27 away from the cap 8, the effect of which is to remove the closure screw 21 from the receiving seat 8b. Finally, the practitioner introduces the closure screw 21 into the connection cavity 22 of the implant 2 and screws it into the internal thread 23 until perfect closure of the connection cavity 22 is obtained. After screwing in the closure screw 21, the practitioner withdraws the screwing tool 27 from the closure screw 21 in order to disconnect the screwing tool from the socket 21b. The closure screw 21 thus prevents the entry of foreign elements into the connection cavity 22 during the phase of osseointegration of the implant 2 in the jaw of the patient.

Good results have been obtained by making the first lateral parts 11a and 11b from a copolymer material, in particular the material manufactured and sold under the name EASTER COPOLYMERE MM211 by the company EASTMAN.

Good results have been obtained by making the second lateral parts 12a and 12b from an elastomeric material manufactured and sold under the name TM4MED by the company KRAIBURG TPE GmbH & Co. KG.

The present invention is not limited to the embodiments that have been explicitly described, and instead it includes the variants and generalizations thereof contained within the scope of the attached claims.

The invention claimed is:

1. Packaging device for a dental implant, comprising:
   a hollow tube having a peripheral lateral wall, a bottom wall and an opening face, which define an internal compartment,
   a cap intended to close the opening face of the tube,
   first means of axial abutment of the implant in the internal compartment,
   first and second means of lateral retention of the implant, which are respectively fixed to two mutually opposite first lateral parts of the peripheral lateral wall,
   wherein at least one of the two first lateral parts is movable between a first position, in which the first and second means of lateral retention of the implant are situated at a first distance from each other, and a second position, in which the first and second means of lateral retention of the implant are situated at a second distance from each other, the second distance being shorter than the first distance.

2. Packaging device according to claim 1, wherein the peripheral lateral wall is continuous, such that the closure of the opening face defines a closed internal compartment.

3. Packaging device according to claim 1,
   wherein:
   the two mutually opposite first lateral parts have a first rigidity, the peripheral lateral wall has second lateral parts that have a second rigidity less than the first rigidity and that are designed and arranged in such a way as to allow the two first lateral parts to move toward or away from each other.

4. Packaging device according to claim 1, having elastic return means for returning the two first lateral parts to the first position.

5. Packaging device according to claim 1, wherein the bottom wall and the two first lateral parts are formed in one piece.

6. Packaging device according to claim 5, having means of interlocking between the first and second lateral parts in order to obtain a continuous peripheral lateral wall after interlocking.

7. Packaging device according to claim 6, wherein the first or second lateral parts have an interlocking groove, while the others of the first or second lateral parts have an interlocking rib.

8. Packaging device according to claim 1, wherein the second lateral parts are in the form of tongues integrally connected to a ring, which is intended to laterally cover free upper ends of the first lateral parts.

9. Packaging device according to claim 1,
wherein:
the first means of axial abutment of the implant have a support plate,
the packaging device has receiving means for said support plate, which receiving means are designed and arranged in such a way as to receive the support plate at different distances from the opening face.

10. Packaging device according to claim 9, wherein the receiving means have a plurality of receiving notches arranged on the internal faces of the first lateral parts.

11. Packaging device according to claim 1, wherein the cap closes the opening face by engaging with force on the hollow tube, and wherein the cap, when it closes the hollow tube, has a lateral overhang with respect to the peripheral lateral wall of the hollow tube.

12. Packaging device according to claim 11, wherein at least one of the first lateral parts has an external groove arranged in line with the lateral overhang of the cap.

13. Packaging device according to claim 1, wherein the cap is dimensioned in such a way that, when the cap closes the opening face of the hollow tube, the cap holds the first and second means of lateral retention of the implant at a distance shorter than the first distance, and preferably equal to the second distance.

14. Packaging device according to claim 1, wherein second means of axial abutment, provided on an internal lower face of the cap, are designed and arranged in such a way as to oppose escape of the implant from the means of lateral retention.

15. Packaging device according to claim 14, wherein the first and second means of axial abutment and the first and second means of lateral retention are made of a biocompatible material.

16. Packaging device according to claim 1, wherein a receiving seat, provided on an internal lower face of the cap, is intended to receive a closure screw for closing the connection cavity of an implant.

17. Packaging device according to claim 1, wherein the second lateral parts are made of an elastomeric material.

18. Packaging device according to claim 1, wherein the first lateral parts are made of a copolymer material.

* * * * *